US005922282A

United States Patent [19]

Ledley

[11] Patent Number: 5,922,282

[45] Date of Patent: Jul. 13, 1999

[54] SUPER FAST TUBERCULOSIS DIAGNOSIS AND SENSITIVITY TESTING METHOD

[76] Inventor: Robert S. Ledley, 1002 La Grande Rd., Silver Spring, Md. 20903

[21] Appl. No.: 08/486,500

[22] Filed: Jun. 7, 1995

[51] Int. Cl.$^6$ .............................. G01N 25/20; C12Q 1/68

[52] U.S. Cl. .................................................. 422/50; 435/6

[58] Field of Search ................................ 250/201; 435/6, 435/5, 7.1–7.9, 287; 382/6; 530/388.1; 364/498

[56] References Cited

FOREIGN PATENT DOCUMENTS

94/25572 1/1994 WIPO .

*Primary Examiner*—Eggerton A. Campbell
*Attorney, Agent, or Firm*—Gary S. Pisner

[57] ABSTRACT

Very rapid diagnosis and sensitivity testing can significantly stem the growing Tuberculosis epidemic in the United States, caused by susceptible AIDs patients and the occurrence of antibiotic resistant mycobacilli. Thus I have invented an automated computerized microscope, the ATBD unit, and slide module to diagnose and test patient's sputum by examining individual living mycobacteria from the patient sample with no culturing required. The diagnosis and sensitivity testing is accomplished in minutes or hours, instead of the current weeks to months. The system inserts a plasmid, specific for *M. tuberculosis,* carrying the luciferase gene into the mycobacteria by improved electroporesis on the slide. Luminescence indicates tuberculosis. Then the mycobacteria are bathed in antibiotics, and if the luminescence is not turned off, the patient's bacteria are resistant. A phage carrying the luciferase gene can also be used to infect the M.TB. Finally, the invention can be applied to any mycobacteriological infection to do diagnosis sensitivity testing even when the species is not known.

43 Claims, 9 Drawing Sheets

$$W' = \frac{W}{\sin\theta}$$

SUPER FAST TUBERCULOSIS DIAGNOSIS AND SENSITIVITY TESTING METHOD

INVENTION

My invention is a complex multi-component apparatus using several technologies in a cross-disciplinary manner, which, in addition to performing very rapid tuberculosis diagnosis and sensitivity, can contribute importantly to establishing a new approach to clinical microbiology.

The purpose of this invention is to automatically be capable of diagnosing tuberculosis and performing antibiotic sensitivity testing on the mycobacteria within hours, rather than taking many weeks or months. This is one of the top objectives of the United States' tuberculosis control and research programs.

NEED AND SIGNIFICANCE TO TB

Public health officials fear a resurgence of Tuberculosis due to AIDS patients, most of whom get Tuberculosis, and also, most importantly, due to the antibiotic resistance being developed by the Tuberculosis mycobacteria themselves. By making the diagnosis and sensitivity testing rapidly, this resurgence can be aborted because patients would be treated on the day that they came for the diagnosis. Otherwise the patients are either hospitalized for at least $800.00 a day while waiting for the diagnosis, or they are let out into the community where they infect others, or they are inappropriately treated with antibiotics before the sensitivity diagnosis is made, which has helped breed resistant bacteria. [1,2] It is a serious and rapidly growing problem, especially due to AIDs patient's vulnerability not only to mycobacterium tuberculosis, but to other types of mycobacteria, such as avium, kansasii, etc.

The rapid increase in TB cases is directly related to the extensive time now required to make the bacteriological diagnosis and sensitivity determination. Shortening the diagnostic and sensitivity testing time to a minimum number of minutes or hours is an important factor in reducing the spread of tuberculosis, hopefully preventing a larger tuberculosis resurgence.

IMPORTANCE OF MY INVENTION

No other method for diagnosing *Mycobacteria tuberculosis* (M.TB), and doing sensitivity testing is comparable to my invention. My invention promises to enable TB diagnosis and sensitivity testing to be accomplished in minutes or hours, rather than weeks or months. This is because my invention does not require any culturing of the mycobacteria, whereas all other methods and proposed methods (except possibly PCR) do require culturing of the mycobacteria, a time consuming process.

In my invention, the individual live mycobacteria are automatically located and identified on the slide by the size and shape of their image. In addition, a plasmid containing the luciferase gene specific for all strains of M.TB, will make only the M.TB luminesce for the diagnosis. For sensitivity testing, the luminescing M.TB are challenged with the antibiotic and if the luminescence is extinguished, the M.TB is sensitive to that antibiotic. All this is automatically observed by my computer controlled instrumentation.

Competing methods for minimizing the time required for diagnosis and sensitivity testing include (a) significant improvement in accelerating the growth of mycobacteria in new medias, (b) the BACTEC, and (c) PCR. This first method can not reduce the time significantly compared with the potential of my new concept because it still is based on developing bacteria cultures. However my method may take advantage of these new growth medias. The BACTEC system still requires bacterial growth, although not necessarily as long as is required from conventional cultures. It inherently requires significantly longer times than the goals of my new concept. The only method that does not require culturing and could compete with my proposal, is the use of polymerase chain reaction (PCR). However, the PCR method is not viable, because the resistance causing gene or genes (in cases where two or more genes are required for resistance) need to be known. Even if the genes are known, the *Mycobacteria tuberculosis* (M.TB) will most likely soon develop other methods for resistance, and again the new mutant gene will have to be discovered, and so forth. Of course, the PCR method would be a great boon for the commercial companies in the field, because they would need continuing ad-infinitum financial support for tracking new genes that produce antibiotic resistance to existing antibiotics, as well as to new antibiotics.

Another possible technique would be to use PCR in a quantitative mode to measure the number of *M. tuberculosis* that are growing in the presence of the antibiotic. But this technique would require culturing the bacteria. Also quantitative PCR is not yet possible according to articles concerning such attempts as reported in the scientific literature.

The advantages of my method for using luciferase on individual bacteria over that of the possibility of using PCR, are clear. My method does not require knowledge of the antibiotic resistance mechanisms; it uses proven, well developed opto-mechanical and biomolecular techniques. Finally, my method utilizes individual bacteria, and not cultures. There can be no faster generally applicable method than observing the viability of individual bacteria with no culturing required.

Overall Concept.

The overall concept is based on the use of an automated pattern recognition microscope, together with the introduction of the luciferase gene into the *Mycobacteria tuberculosis* (M.TB) by means of a specific plasmid. Then each transformed bacteria will luminesce and the diagnosis can be made. The time required is short, about 5 to 10 minutes.

Next, the luminescing bacteria are challenged by the various antibiotics, and it is observed whether or not the light is "turned off", i.e. whether the bacteria are killed. The time required depends on the mode of action of the antibiotic. If it interferes with a vital part of the bacteria's metabolism, then the bacteria will be killed rapidly, possibly within minutes; if it interferes with the reproduction functions of the bacteria, it will take more time, possibly a number of hours.

Thus my instrument carries out the following steps:

1) The sputum or body fluid sample of the patient is prepared as is currently done, and placed on a special glass slide. The bacteria are immobilized on the slide by being trapped in the pores of a $5\mu$ filter. This slide is automatically scanned by my instrument and within 3–5 minutes, all of the mycobacteria are located and their coordinates recorded by the computer so that each can be later relocated.

2) The plasmid containing the luciferase gene is inserted into the mycobacteria on the slide by means of a process called electroporesis. These plasmids will be formulated to enter the M.TB cells. These cells will then be the only ones to luminesce. This procedure is expected to take about 5–10 minutes. An alternative method makes use of bacteriophage and another method uses immunofluorescence coupled with plasmids.

3) The instrument will then relocate each of the mycobacteria found and check for those that are luminescing. Luminescing bacterial cells indicate a positive Tuberculosis diagnosis. These bacteria will then be used for the sensitivity testing part of the process.

4) Antibiotic will be added to the slide and after a known prescribed time, that can vary from 1 minute to six or more hours, depending on the particular antibiotic, the mycobacteria will again be automatically relocated by the instrument. If the light is still on, then the bacteria are resistant; if the light is off then the mycobacteria are sensitive to the antibiotic. In my initial design, eight different antibiotics will be tested simultaneously on the same slide.

The instrumentation consists of three aspects: (a) The mycobiological aspects, including the preparation of the sample, use of the plasmid, and use of electroporesis; (b) the hardware portion, is a microscope and computer controlled motorized stage, as well as sensitive television cameras and photomultiplier detectors; and (c) the software portion, consisting of a series of computer programs run on a PC to control the motorized stage, carry out the pattern recognition required, etc.

New Approach to Microbiology.

Current methods in microbiology depend on growing colonies of bacteria in various culture media on agar plates or in broth filled test tubes. Then a diagnosis is made and/or sensitivity to various antibiotics is determined, by observing the growth in the various culture media, and/or by observing the appearance of the colonies, and/or by making measurements of other physical or chemical characteristics of the colonies. Millions of bacteria make up a colony and the colony is treated as a single entity. Of course the bacteria may be observed through a microscope, but by and large, the real information concerning the existence of the bacteria, the nature of the bacteria, and their characteristics is determined by culture growth medium and colony appearance and manipulation.

The objective of my new approach is to work with individual bacterium from the specimen. For then the culture time will be eliminated. This is of particular importance with respect to the mycobacteria, that inherently grow very slowly. The new concept is to use each individual bacterium itself as a “micro test tube”. Practically all the chemical reactions of importance will, of course, take place within the bacterial cell. The problem then becomes one of, first, locating the bacterial cell, bathing it in the desired media, and detecting the results from the individual cell. The goal is not to have to wait for the bacteria to divide, but to just handle a small number, say less than 100 to 1,000, of individual bacteria by direct means. In concept, the results will be obtained within a very short period of time.

To carry out such a procedure, a special computer controlled automated microscope is used, here denoted as the “Automated Tuberculosis Diagnosis Unit” or ATBD unit. For each of the steps to be carried out by the ATBD unit, the image and light being detected travels through a number of different pathways. The process is controlled by a computer. For handling the mycobacteria themselves, a special microscope slide is used that contains a number of identical modules, where each module is used for testing a different antibiotic.

PREFERRED EMBODIMENT OF THE ATBD UNIT

Figure 1:
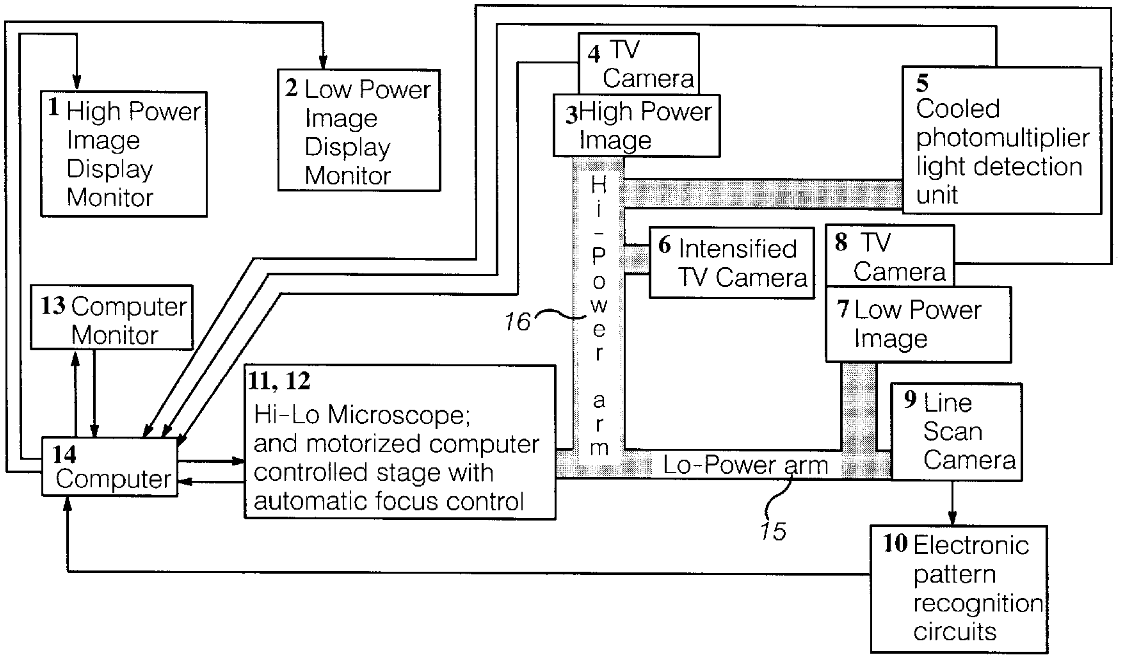
FIG. 1 is a block diagram of all possible components of the apparatus of the invention.

Preparing the Sputum Samples (Standard technique, well known)

Samples will be liquified and decontaminated using N-acetyl cysteine/NaOH and concentrated by centrifugation following standard mycobacteriology laboratory procedures, such as that used at the Georgetown University Hospital (GUH). Sediment containing the mycobacteria will be suspended in 10% glycerol, transferred to a microcentrifuge tube, and centrifuged for 1 min. This will be repeated twice, and the final pellet will be suspended in 10% glycerol to provide a suspension suitable for electroporation. For instance, the standard mycobacteriology laboratory procedure at GUH (see references #3 for details) includes:

(i) Preparing the reagents: (A) N-acetyl-L cysteine/sodium hydroxide; (B) 0.676 M phosphate buffer; and (C) PANTA PLUS Kit (optional for my purposes)—Antimicrobial and growth supplement BD Catalog #04764.

(ii) Collecting the specimens. Three to five early morning sputum specimens are collected in sterile containers, 5 to 10 ml.

(iii) Processing the specimens. The specimens are processed as follows: (A) Using a Maximum of 10 ml of specimen in a sterile blue-capped 50 ml centrifuge tube, add an equal volume of freshly prepared (within 24 hours) NALC/NaOH solution to each specimen; (B) Vortex each specimen vigorously for 30 seconds; (C) Allow the specimens to sit for 15 minutes; (D) QS (Quantity Specimen) each specimen to 50ml with phosphate buffer; (E) Invert each tube to mix the solutions and stop the digestion; (F) Centrifuge the tubes for 15 minutes at 3,600 g; (G) Decant the supernatant from each tube into a splash proof container; and (H) Resuspend the sediment in 1–2 ml of sterile deionized, distilled $H_2O$ and Prepare sides.

Luminescence.

The electroporation of the 10% glycerol solution containing the M.TB is accomplished. Then to see luminescence, the 10% glycerol solution is replaced with 7H9 broth with 10% ADC enrichment (complete 8H9) to allow recovery of cells for expression of luciferase. Broth will then be replaced with luciferase buffer containing luciferin (promega Luciferase Assay Kit). The technique for making the mycobacteria luminesce is adapted directly from the work of Dr. Crawford, and also from the work of Drs. Jacob and Bloom, including the use of electroporation for the plasmids. The luciferase catalyzes the following reaction [4]:

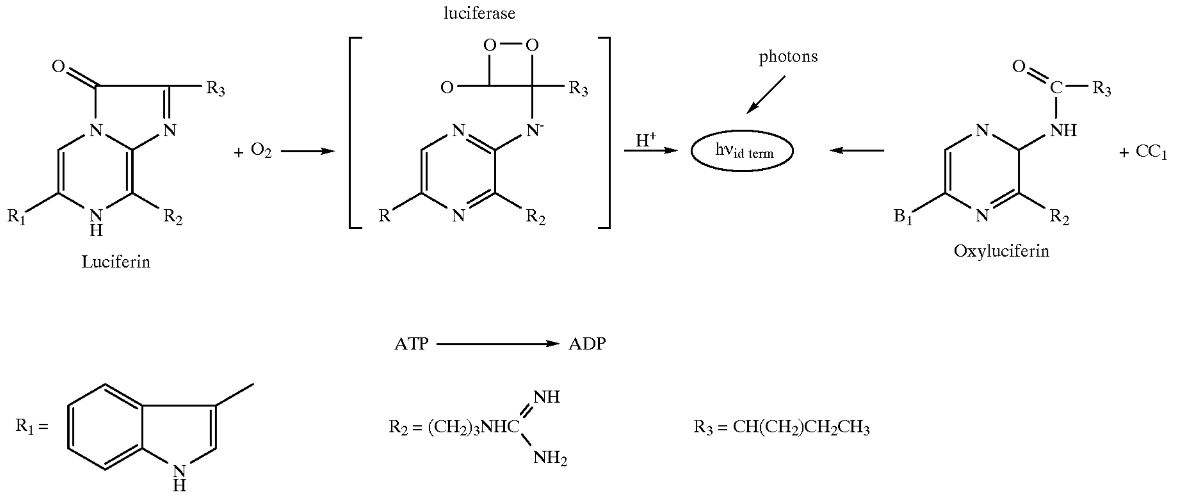

Luciferin

Oxyluciferin $R_3 = CH(CH_2)CH_2CH_3$

Specifically, luciferase in the presence of ATP, $MG^{2++}$, and $0_2$, oxidizes luciferin through an intermediate compound, luciferyl AMP, to produce oxyluciferin, AMP, PP, $CO_2$, and light (photons). To do the sensitivity testing, this broth will be replaced with 7H9 broth containing the test drug. After incubation for the appropriate time required for each particular antibiotic, the broth will again be replaced with the luciferase buffer containing luciferin and the luciferase activity will be measured. The luminescence will occur immediately and will last until the luciferin is used up.

Developing a plasmid specific for M.TB.

The currently used luciferase plasmid constructs are based on the origin of replication of plasmid pAL5000. They have been shown to be stably replicated and capable of expressing luciferase in *M. smegmatis,* and in a series of M.TB isolates. This plasmid has also been introduced into *M. avium* and high levels of expression of luciferase have been obtained. In their present form these plasmids can be used for drug susceptibility testing. However, in order to provide a specific detection of M.TB in clinical samples it is necessary to construct a plasmid that is specific for M.TB. There are two possible approaches—construction of a plasmid that is capable of replication only in M.TB or development of an expression system that expresses luciferase only in M.TB.

There have been no naturally occurring plasmids identified in M.TB. While it may be possible to engineer a plasmid such that replication is dependent upon some M.TB specific function, the current state of knowledge of plasmid replication in mycobacteria is not sufficient for this approach. It is more likely that with the expanding knowledge of gene expression in M.TB, the luciferase gene for expression in M.TB can be engineered. This requires the identification of an M.TB specific gene, and the use of regulatory elements of that gene for control of luciferase production. Given the current state of research on M.TB it is very likely that such a gene will be identified. (see reference 5 and 6).

Improving the electroporation efficiency.

The mechanism of the electroporesis as currently understood in the field is shown in FIG. 9. After the luciferase gene is incorporated into the plasmid (a) these plasmids are added to the suspension of mycobacteria (b) next a voltage pulse is applied through the suspension by a pair of electrodes (where only the top electrode is shown in the diagram). A current makes a small hole in the cell membrane of the mycobacteria (c and d) and a plasmid enters the bacteria through the hole (d and e). Once inside the bacteria (e), the plasmid will catalyze the chemical reaction to make luciferin, thereby causing the bacteria to luminesce (f).

I optimize the electroporesis procedure by adjusting factors not heretofore studied in the field. I improve the efficiency of transforming the M.TB by several orders of magnitude or more. Presently, for plasmids, only the electroporesis voltage has been optimized, but not the geometrical considerations involved. In fact even the current use of the word "efficiency of transformation" of the bacteria is defined differently from my needs. At present, 'efficiency' refers to the number of transformations per $\mu$ gram of plasmid DNA, whereas I am interested in the 'efficiency' defined as the number of bacteria transformed per 100 bacteria, i.e. the percent of the bacteria transformed. To my knowledge this has never been measured.

Concerning my optimizing the electroporation process, I first use a modest static electric field to rotate the bacteria to a position approximately perpendicular to the electrodes as far as the 5$\mu$ filter pores will allow. It is well known that microscopic particles tend to align their lengths along the direction of an electrostatic field. This makes an end of the ellipsoidal shaped bacterial cell either touch or move closer to the electroporesis cover slip electrode. The bacteria are bathed in a dielectric solution (e.g. 10% glycerol, 90% deionized distilled $H_2O$.) Thus the minimum resistance path between the electrodes then includes a segment through the cytoplasm along the length of the bacteria because of their orientation, encouraging the electrical current of the pulse to pass through the bacteria. The current enters the bacterial cell at the part closest to the coverslip electrode. Since this end part of the cellular membrane has the greatest curvature, it is also under the greatest strain, and hence is most vulnerable to being punctured by the applied electrical pulse of the electroporesis process. It is thought that through such a puncture hole the plasmid enters the cell. No such mechanism has heretofore been made.

As illustrated in FIG. 9, I first apply an electrostatic field across the suspension, causing the mycobacteria to align themselves so that their long axis is perpendicular to the electrode (g). Then the voltage pulse is applied (h), the hole is made (i), the plasmid enters the bacteria (i & j) and the bacteria luminesces(k).

Alternative methods: Use of immunofluorescence coupled with mycobacteria phage (not specific to M.TB): use of bacteriophage specific for M.TB.

Presently M.TB is identified by an antibody-antigen reaction with a specific protein on the M.TB cell wall, where the antibody has an attached fluorescent molecule. Thus using such immunofluorescence, all of the M.TB and only the M.TB can be identified under fluorescent microscopy and the x,y location of each M.TB bacteria on the slide can be recorded. If the UV or other stimulating light is now turned off, there will no longer by any fluorescence. There already exists a plasmid that can insert the luciferase gene into all mycobacteria (not specific to M.TB). This plasmid is utilized and makes all the mycobacteria luminesce, including the M.TB locations of which have previously been specifically recorded. Luminescence is then easily and automatically verified by relocating each of the individual M.TB bacteria by means of the computer-controlled microscope. Then after the antibiotics are applied, the automated microscope can again relocate each individual M.TB bacteria and evaluate the continuing luminescence of only these particular M.TB bacteria to assess the M.TB sensitivity. Researchers are attempting to develop a lysogenic bacteriophage that will select only M.TB to infect. Such a phage will then be adapted to carry the luciferase gene into the bacteria. If successful, then this phage can be used as described for plasmids.

A lysogenic phage, mycobacterium phage L5 already can infect mycobacterium but is not specific to M.TB. It can be made to carry the luciferase gene into the mycobacteria as can the plasmid discussed above. Then the immunofluorescence method coupled with the mycobacterium phage L5 can be used in an analogous manner to the mycobacterial plasmid.

Components and functions of the ATBD unit.

The hardware of the ATBD unit essentially consists of a computer controlled microscope having multiple capabilities associated with the multiple light pathways involved. Extensive use is made of the Hi-Lo microscope principle, invented and patented by R. S. Ledley, and of the method for scanning at very high speeds and automatically detecting, recognizing, and locating all objects on a conventional glass slide within three to five minutes, also developed by R. S. Ledley and his group [7,8,9,10,11]. These results from my previous developments are used, because mycobacteria are about 5μ in length, only about half the length of objects previously observed, and ½μ in width, only about half the width of objects previously observed. The three main capabilities of the ATBD unit are as follows: (1) to scan the modules of the slide and detect, recognize, and list the x,y coordinates of all the mycobacteria; (2) to relocate under the objective lens for processing or operator viewing each mycobacterium found; (3) to detect whether or not a mycobacterium is luminescing.

Optical design.

Because of its optical design, the ATBD unit can form simultaneous images of different magnifications, all arising from a single high power objective lens of high numerical aperture (N.A.), e.g. 100×, 1.4 N.A objective. The simultaneous images can have field diameter ratios of as much as 1:10 (or field area ratios of as much as 1:100). For example, from a single 100×N.A. 1.4 objective, the Hi-Lo optics can produce both a 50μ diameter image and a 500μ diameter image at the same time, where both images are formed with the resolution of 1.4 NA objective. In the optical system the light beam containing the image is split into a Hi-power arm path, and a Lo-power arm path, see FIG. 1. The Lo-power arm has two ports, for the line scan camera, and for the Lo-power image TV camera. The Hi-power arm path has three ports, for the Hi-power image TV camera, for the photomultiplier tube very low-light detector, and for the image-intensified TV camera. Two TV monitors are used, one for the Hi-power image, and the other for the simultaneous Lo-power image. (In the future I will determine whether or not to use the image-intensified TV camera.) All the lenses of the Hi-Lo microscope are purchased from commercial companies, namely Olympus, Kodak, Vivitar, and Hoya. The Dage TV camera and the Fairchild line scan camera are used.

Focus control.

The ATBD unit also includes an instantaneous automated focus control of my own invention, which keeps a Lo-power image in focus to within 2 to 6μ accuracy while scanning the slide. In addition the ATBD unit includes a motorized focus control, activated either by manual interaction through the computer or by the use of automatic focus control circuitry, which keeps a low-power image in focus to within ½μ accuracy. The instantaneous focus control is used during the high speed mycobacteria detection and recognition procedure, whereas the interactive and circuitry focus control is used during with the Hi-power image for operator viewing and luminescence detection.

The computer control.

The ATBD computer performs multiple functions: it controls the motion of the motorized stage; assists the pattern recognition circuitry in recognizing and distinguishing the mycobacteria from other objects on the slide; records the x, y coordinates of each mycobacterium and stores them for the procedure of relocating them under the objective lens; controls the steps to be taken during the procedure; produces prompts for the operator at the proper times; enables operator interaction during the procedure; analyzes the results; and prints out a report for each patient.

The microscope slide and modular reaction chambers.

For a normal sized glass slide, which is usually 50.8 mm by 25.4 mm (i.e. 2 inches by 1 inch), the useful area to be scanned is generally only 25.4 mm by 19.05 mm (that is 1 inch by 0.75 inches). The microscope stage is automatically moved under the objective lens in a systematic pattern, enabling the line scan camera to pass over successive strips on the slide area (see FIG. 6). The line scanner element sees a line of 400μ in length, with 1024 pixels along the line, and one pixel wide. Each scan strip is 24.4 mm long, and 400μ wide. Altogether there will be 19.05 mm/0.4 mm=47 strips scanned. Going in 5μ steps, at a rate of 834 steps/second, produces a speed of 4,170 μ/sec. Thus the length of 25.4 mm, or 25,400μ is covered in 6.09 seconds and for the 47 scanned strips, I have (47×6.09)/60=4.77 minutes. However for my glass slide with the modular chambers (see FIG. 2), only the chambers need be scanned. Although the slide is larger than the usual glass slide, a smaller percentage of the area need be scanned and hence the time required for the scan of a slide is roughly of the same order of magnitude as just calculated. The x,y coordinates of any mycobacterium on a particular slide are recorded in the computers memory as associated with that slide so that at a later time that particular slide can be put back and the ATBD unit can very rapidly relocate the bacterium with the motorized stage. A TV camera can be used instead of the line scan camera. The microscope stage is then moved in successive fields of view. Each field of view is 400μ×400μ, making about 83 fields in a strip.

Figures 1, 2A:
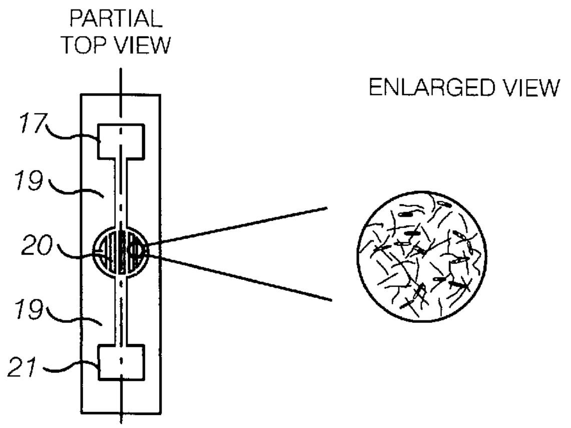
Figure 2B:
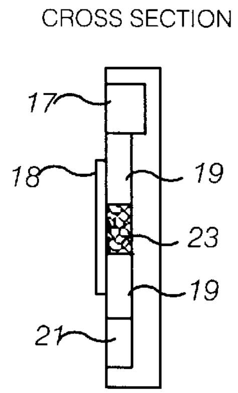
FIG. 2 is a diagram of a preferred embodiment of the improved electroporesis or reaction chamber showing the case of a plurality of eight modules, where each module has a source or output well, capillary canals or channels, material or filter in the reaction chamber, and a sink or output well.
Figure 2C:
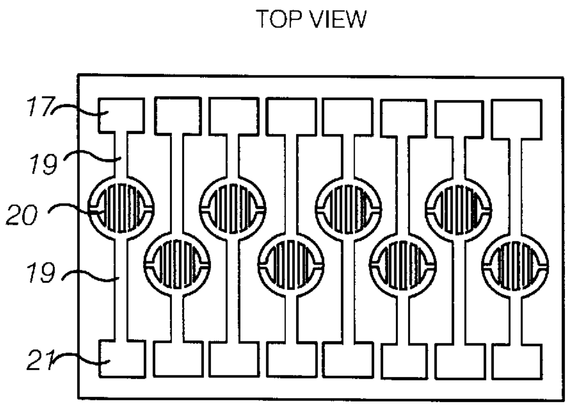

A reaction chamber module consists of five parts as shown in FIG. 2: the reagent source-well, the reagent-in canal, the reaction chamber itself, the reagent-out canal, and the reagent sink-well. Capillary action moves the reagents from the source-well through the reaction chamber to the sink-well, as the source-well is emptied and the sink-well is filled. The in-out canals and the chamber are covered with a thin cover glass. The source-well can be filled with a pipette, and the sink-well can be emptied with a pipette or sponge. Initially this filling and emptying will be accomplished manually and will be used for nonpathogenic bacteria, but it can also be automated. For the actual pathogens, i.e. M.TB, a much more elaborate system with appropriate safeguards will be developed.

Figure 8:
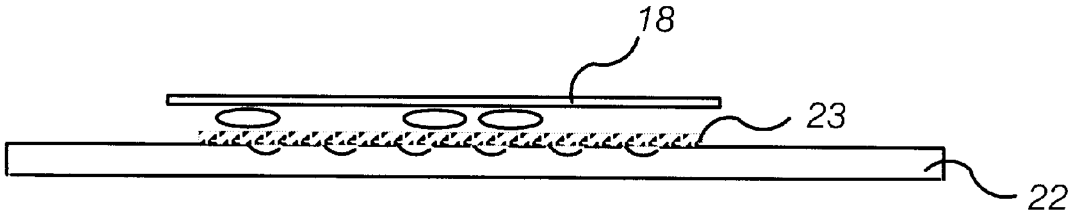
FIG. 8 is a diagrammatic detail of the reaction chamber of a module where the “coverglass” acts as one electrode, and the “glass slide” acts as the other electrode, and the grooves in the “glass” surface carry the reagents.
Figure 9A:
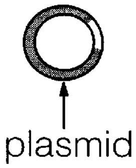
FIG. 9 reviews diagrammatically the process of electroporation improvement.
Figure 9B:
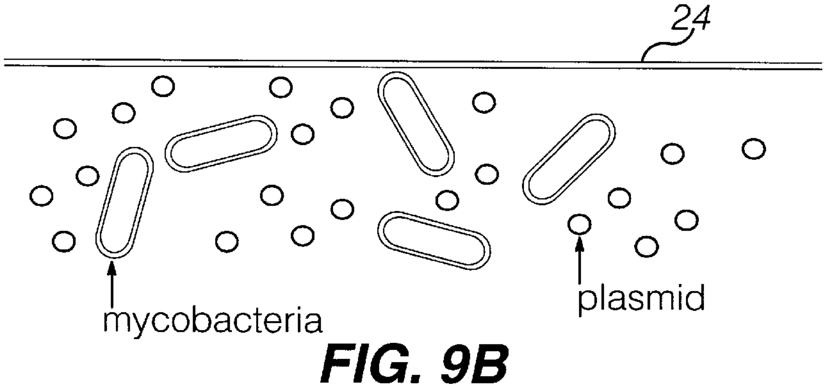
Figure 9C:
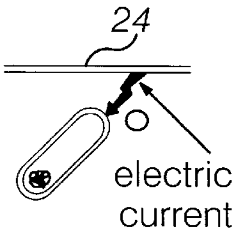
Figure 9D:
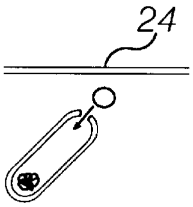
Figure 9E:
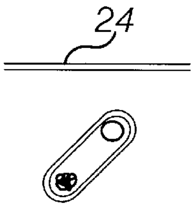
Figure 9F:
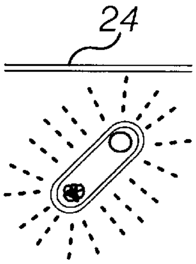
Figure 9G:
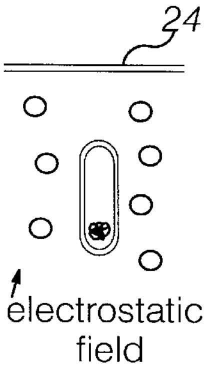
Figure 9H:
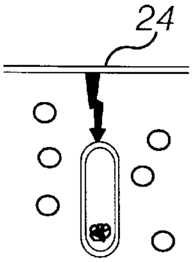
Figure 9I:
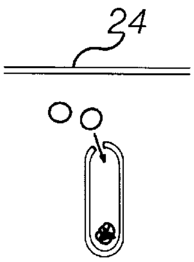
Figure 9J:
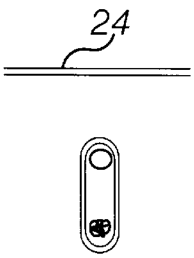
Figure 9K:
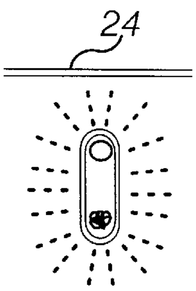

The reaction chamber itself is designed to carry out the following functions: (1) immobilize the mycobacteria, (2) bathe the mycobacteria in the reagents required for each step in the process, and (3) perform the electroporesis. These functions are carried out as follows: the chamber is filled with a filter having 2.5$\mu$ and 5$\mu$ pores on top of which the mycobacteria lie. Thus a sandwich is made, composed of the glass chamber bottom, the filter, and the coverglass on top, with the mycobacteria trapped between the filter and the coverglass, in the filter pores (see FIG. 8). The bottom of the well will be made of conducting glass, as will also be the composition of the cover glass; these will be the electrodes for the electroporesis action. The filter will transport the reagents through the reaction chamber; the filter pores will immobilize the mycobacteria. The thickness of the filter, that is the distance between the chamber bottom electrode and the top cover glass electrode, will be about half a millimeter. This design enables all three functions of the reaction chamber to be efficiently carried out.

Electroporation circuits.

Figure 3:
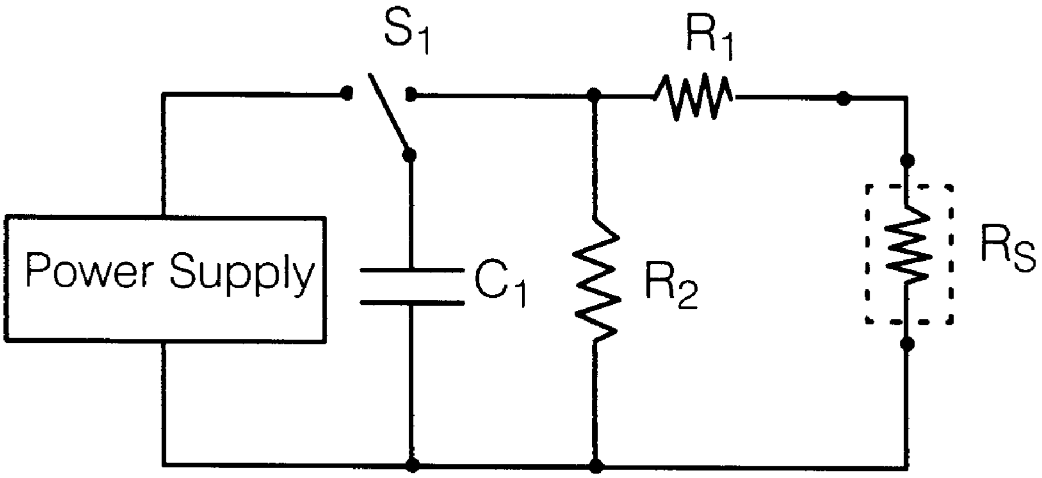
FIG. 3 is a typical electroporesis pulse circuit.

The most common electroporation circuit is shown in FIG. 3. When switch $S_1$ is switched to the power supply, capacitor $C_1$ is charged up. When $S_1$ is switched to the load, $C_1$ discharges through the total resistance $R_T$ which consists of resistor R2 in parallel with resistor R1 in series with the resistance $R_S$ of the sample. R1 is merely to protect $C_1$ and $S_1$ should an arc occur in the sample. R1 is usually on the order of 20Ω. R2 is usually much smaller than $R_S$ and usually determines the total load resistance.

Figure 4:
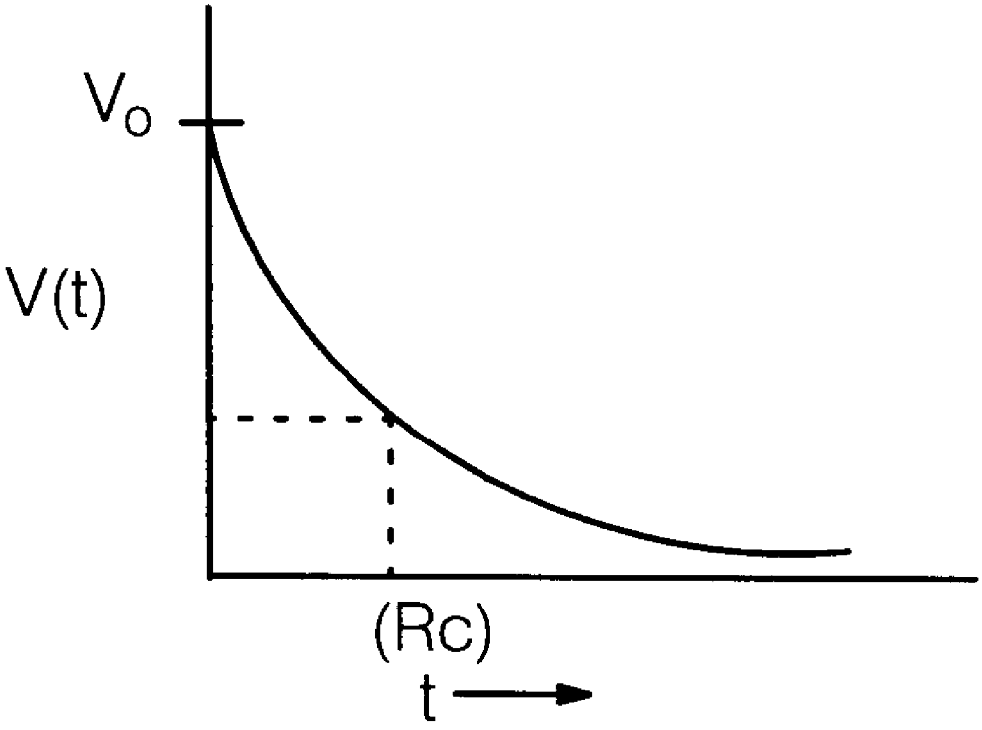
FIG. 4 shows the shape of a typical electroporesis discharge.

The circuit of FIG. 3 produces an exponentially decaying voltage, as shown in FIG. 4, across the sample. The advantage is that the power supply can charge the capacitor over a long period of time and then expend this energy in the sample in a short time. Since the total resistance $R_T=[R_2\times(R_1+R_S)]/[R_2+(R_1+R_S)]$ then the exponential voltage decay is given by $V(t)=V_0\exp(-t/R_TC_1)$ where $V_0$ is the voltage, t is the time from $t_0$ when $S_1$ was switched to the load and exp stands for the natural log base e raised to the power inside the parentheses. $R_TC_1$ is referred to as the time constant. When the time t equals $R_TC_1$ the voltage has decreased to 37% of its original value $V_0$.

In a typical electroporation procedure, the following values might be used: $R_S$=5000Ω, $R_1$=20Ω, $R_2$=400Ω, $C_1$=2 $\mu$F. Then by the first equation $R_T=(400\times5020)/(400+5020)=370.5\Omega$, and $R_TC_1$=0.74 msec. It can be seen from this example that when the sample resistance is large compared to $R_2$, the time constant will be mostly determined by $R_2$.

The luminescence detection systems.

The ATBD unit includes in the Hi-power path both a photomultiplier port and an image intensified or a cooled low light television camera port (both shown in diagram). The photomultiplier tube is an extremely sensitive light detector. The noise inherent in a photomultiplier tube is proportional to the second power of the absolute (Kelvin) temperature (i.e. $T^2{}_K$). Thus cooling the tube can substantially decrease the noise, or increase the signal to noise ratio. Alternatively, very low light images can be formed using intensified or cooled TV cameras. These are commonly used by the military for night vision purposes. However, even non-intensified TV cameras image a luminescing mycobacteria and also non-cooled photomultipliers relatively rapidly detect the light from a single mycobacterium.

Photomultiplier detection.

In using the photomultiplier for detecting the luminescence integration of the output current is used, rather than counting the photon "events". The quantum efficiency of a PMT is $(N_k/N_{ph})$'100 where $N_k$ is the number of electrons emitted and $N_{ph}$ the number of incident photons. The gain of a PMT, $\mu=N_p/N_k$ where $N_p$ is the total number of electrons reaching the anode. For example, for a KM 3054-20 Dumont tube, the gain is 300,000 and the dark current is 1 Na at 25 degrees centigrade with no light into the tube. Since the charge on an electron is $1.602\times10^{-19}$ coulombs the number of electrons per second dark current is $1\times10^{-9}/(300.00\times1.602\times10^{-19})$=20,807 electrons per second. Of course it is the dark current that limits the sensitivity of the tube, and to improve the sensitivity, the dark current should be minimized. If the quantum efficiency were 1 then this would correspond to 20,807 photons per second. However, the quantum efficiency is usually less than 1. But, the dark current $i_t=1.20\times10^2\times T^2\times\exp(-1.16\times10^4\phi_t/T)$ amp per $cm^2$, where T=the absolute temperature in degrees Kelvin and $\phi_t$ is the thermal work function for the cathode material. Therefore, cooling the tube will clearly have a great effect on substantially lowering the dark current and therefore improving the sensitivity of the tube.

According to Jacobs et al. [12], the luciferase catalyzes the luciferin and ATP reaction to generate 0.85 photons per molecule reacted. Presuming several hundred thousand molecules are involved per second, I would expect the luminescence to contain over 85,000 photons per second. These calculations also confirm that there is no problem in detecting the luminescing intensity of the mycobacteria without cooling the photomultiplier.

System functions and software.

Figure 5:
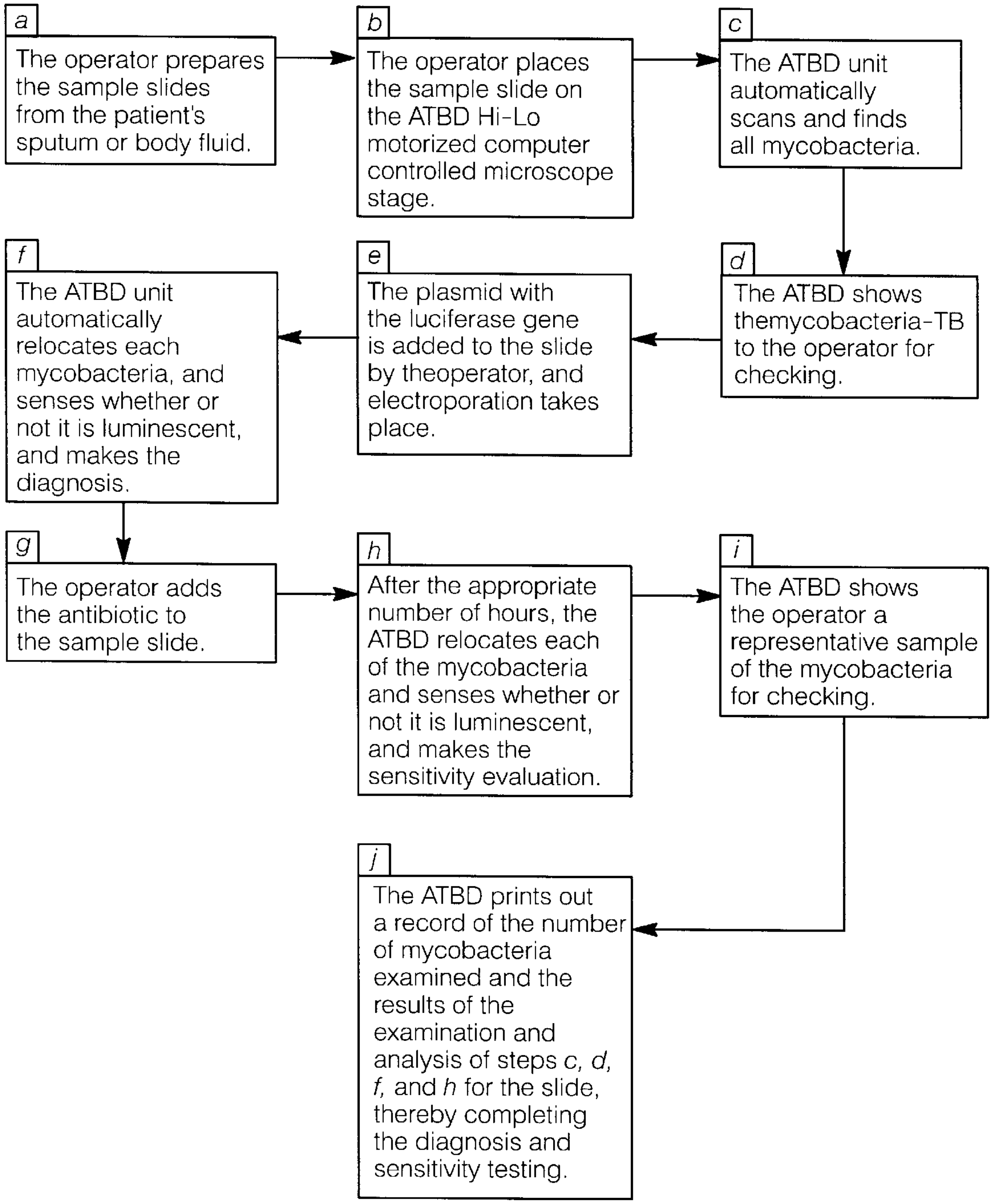
FIG. 5 is a functional flow chart for the use of the ATBD apparatus identifying automated and operator interactive functions.

The purpose of the software system is to (a) run the ATBD unit, (b) enable operator interaction, (c) keep track of the results on the individual bacteria, (d) prompt the operator for inputting reagents and for disposing of effluents, (e) tally the results and perform the analysis, (f) prepare patient reports, (g) print images. FIG. 5 shows the overall functional block diagram.

In this block diagram, boxes a, b, e, and g are carried out by the operator; boxes d and i represent the operator-ATBD unit interaction parts of the process; and boxes c, f, h, and j are the entirely automatic functions performed by the ATBD unit. In the future some of the operator functions, namely that of sputum or patient specimen preparation, adding reagents, etc., can also be easily automated. The operator-ATBD unit interaction steps could be eliminated after a while, but these are essential in the initial clinical testing by a customer of the ATBD unit, in gaining the confidence of the user in the proper functioning of the ATBD unit, as well as in demonstrating the effectiveness of the ATBD unit. The entirely automatic functions of the ATBD unit are, of course, most critical for minimizing the time required to make a diagnosis and carry out sensitivity testing.

Standards for making a diagnosis.

The American Thoracic Society Diagnostic standards are used for diagnostic criteria (see table 2 taken from a current textbook). Table 2 gives standards for making a manual diagnosis of tuberculosis by examining the microscopic field directly, in terms of the average number of mycobacteria seen per n fields. For example a 1+ diagnostic level holds if the microscopist sees on the average between 1 to 9 bacteria when examining 100 fields (say at 100× objective). As described above for the conventional glass slide, the ATBD unit would scan about 20 stripes, each 400 p wide and say 25,000$\mu$ long, giving a scanned area of 25,000×400×20≈200,000,000$\mu$, I would have 80,000 fields (at 50$\mu$×50$\mu$=2,500$\mu^2$ per field) scanned on the slide. Thus the number of mycobacteria associated with each diagnostic level can be calculated as shown in Table 3.

Therefore to make the diagnosis, the ATBD unit is directed to scan the entire slide where the patient samples are located, i.e., in the reaction chambers of the modules. Although the reaction chambers of the slide modules are of a different shape than the slide dimensions on which my calculations are based, the combined area of the chambers will approximate the area of the calculations. For the diagnosis all chambers will be used; for the antibiotic sensitivity, each chamber will be used for a specific antibiotic. Up to eight different antibiotics can be tested on a slide at the same time, one for each chamber.

TABLE 2

Method for Reporting Numbers of mycobacteria Mycobacilli Observed*)

| # of Bacilli Observed | CDC Method Report | |
|---|---|---|
| 0 | Negative | (–) |
| 1–2/300 fields | Number seen† | (±) |
| 1–9/100 fields | Average no./100 fields | (1+) |
| 1–9/10 fields | Average no./10 fields | (2+) |
| 1–9/field | Average no./field | (3+) |
| Greater than 9/field | Greater than 9/field | (4+) |

*Examination at ×800 to ×1000 is assumed. (American Thoracic Society: Diagnostic standards and classification of tuberculosis and other mycobacterial diseases. Am Rev Respir Dit 123:343–358, 1981)

†Counts less than 3/3000 fields at ×800 to ×100 are not considered positive; another specimen (or repeat smear of same specimen) should be processed if available.

TABLE 3

Number of to be seen by the ATBD unit for a diagnosis.

| No. of Areas | Average # bacteria/slide | diag |
|---|---|---|
| 80,000 ÷ 300 = 266 areas | 266–532 | ± |
| 80,000 ÷ 100 = 800 areas | 800–7,200 | 1+ |
| 80,000 ÷ 10 = 8,000 areas | 8,000–72,000 | 2+ |
| greater than 9/field | over 720,000 | 4+ |
| less than 3/3,000 fields or under 39 per slide are considered negative | | |

ATBD unit diagnosis and sensitivity testing.

To make a specific diagnosis of M.TB, a plasmid or bacteriophage specific for M.TB is used, in which case only these bacteria will luminesce. Alternatively the M.TB can be identified by immunofluorescence as described above. Thus the diagnosis of tuberculosis can be accomplished by the ATBD unit in accordance with Tables 2 and 3. This step will take no longer than 20 minutes. This step (see box f of FIG. 5) requires the ATBD unit to determine the number of luminescing M.TB cells in a 50$\mu$ diameter field. For the intensified TV camera (number 6 in FIG. 1) the images can be easily counted in each field viewed. For the photomultiplier light detection unit (number 5 in FIG. 1) the integrated light output can be converted into the equivalent number of luminescing cells. As with many biomedical automated pattern recognition applications, initially the clinician wants to check the system during operation. (see FIG. 5.) Therefore the operator may direct the computer to relocate the mycobacteria, one at a time, for viewing by the operator at high power, for confirmation, box d. Of course where thousands of mycobacteria are in the patients fluid sample, the operator will view a random sample. Similarly each luminescing mycobacteria found can be shown, box f.

Again the operator may want to check the ATBD unit, by observing the same bacteria after antibiotic exposure, box i. Finally, the results will be statistical such as the standards for the diagnosis of tuberculosis was. The ATBD unit develops the averages per field in a similar manner. However the mycobiologist defines the meaning of the results. Since such data have not heretofore been available, the sensitivity in these terms is not now defined, i.e., what percentage of the mycobacteria must be killed in order to make a sensitivity determination. For example, rifampin and streptomycin inhibit protein and DNA synthesis and therefore only take a few hours to kill the bacteria. On the other hand, isoniazid and ethambutol inhibits cell wall synthesis, among other things, and therefore can take overnight to kill the bacteria. Of course while the antibiotic is working on the bacteria, the microscope slide can be removed from the ATBD unit and put into an incubator elsewhere. After the prescribed amount of time, the slide is replaced in the ATBD unit and the individual bacteria relocated for observation.

As stated above, the ATBD unit locates living mycobacteria. The use of a Heine condenser, a clever device that was manufactured by Leitz, can be used for flexibility in obtaining phase, darkfield, or a combination of both to optically enhance the image, and/or some vital stain, like Methylene blue can be used.

Uses of these methods for other mycobacteriological diseases.

In addition to tuberculosis, other diseases such as lepracy, bovine tuberculosis, *M. avium* infection, etc. can occur in humans as well as in animals. Mycobacteria is the genus, and *M. tuberculosis, M. leprae, M. bovis, M. avium,* etc. are the species, that cause the corresponding diseases. The methods of my invention are also applicable to these other diseases, in addition to tuberculosis. Although it is best to diagnose the specific species causing the patients disease, to initiate therapy all that is required is the results of antibiotic sensitivity tests. For this purpose it would not be necessary to have a plasmid or a phage specific for the particular species involved.

For the broad generic or genus diagnosis, a plasmid or a phage may not exist that can insert the luciferase gene into all the species of the mycobacteria genus. In such a case, automatic pattern recognition (PR) is the only method that can be reliably used. This method identifies the location of all the mycobacteria viewed under the microscope. Then a mycobacteria plasmid or mycobacteria phage can be used to get the luciferase gene into the mycobacteria cells. The results can be checked by observing any luminescence at the previously PR located mycobacteria positions. If there are luminescing mycobacteria then sensitivity testing can be accomplished.

Automated pattern recognition aspects.

Figure 6A:
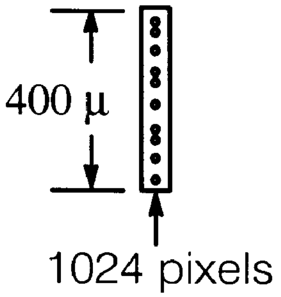
FIG. 6 shows the path of the line element of the line scan camera.
Figure 6B:
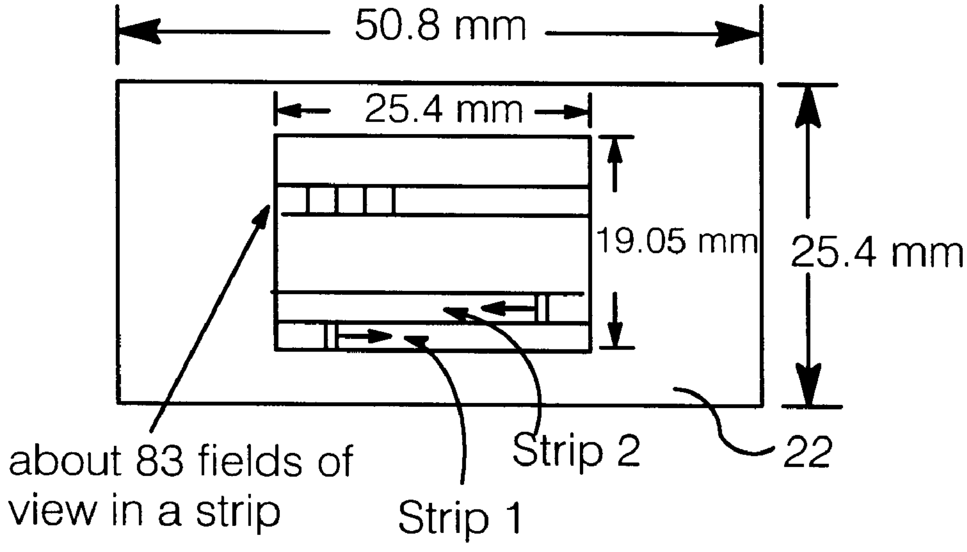
Figure 7A:
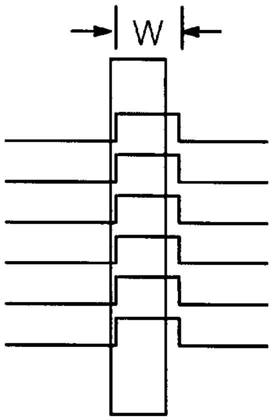
FIG. 7 illustrates the use of “covers” to recognize mycobacteria but no recognize a cell.
Figure 7B:
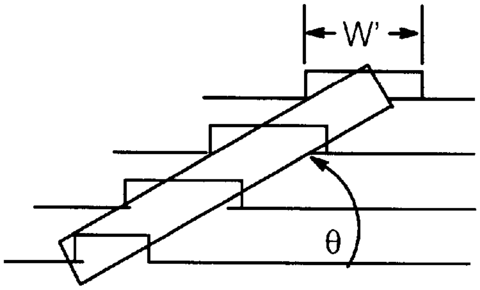
Figure 7C:
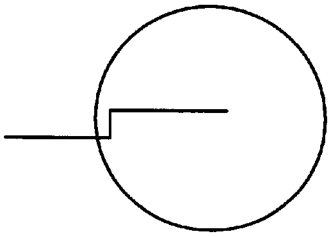

The TV camera or line scan camera scans successive microscopic fields of view forming a strip (see FIG. 6*b*) of width of 400 microns with 1024 pixels (see FIG. 6*a*). For the TV camera, as each field of view is scanned the microscope stage successively move to the next field of view. For the line scan camera, the stage moves continuously under the line scan element to form the successive fields of view. The electronic pattern recognition circuits will perform an algorithm similar to FIG. 7. Here I have drawn the mycobacterium as a rectangle. As each pixel of the line scan camera crosses a bacterium, a "cover" is formed and the cover ends when the scan go past the bacterium as shown in FIG. 7(*a*). Of course the bacterium will be at random angles as shown in FIG. 7(*b*) and the covers will be longer. The collection of covers identifies the bacterium. Only if the width W or W' is within the appropriate range of length, and if the collection is aligned appropriately, and other features of the cover collection also exist, will the collection be called a mycobacterium. Other objects that are too large, such as is shown in FIG. 7(*c*), will not be considered a bacterium because the cover might be too long or too short, or the collection might vary in length by too much or might not be aligned appropriately, etc. Of course, the actual algorithm to be used is more complex than this simplified description, but the details would take too much space here and are not appropriate to include. However, I can state that the identification of a mycobacteria is accomplished in part by hardware and in part by software. The hardware determines the coordinates of the start of a cover and the end of a cover in real scanning time, and transmits these results to the computer through a DMA (direct memory access) computer interface. All of these electronic capabilities are of my own design. Similarly for a chain of mycobacteria the start and end of the chain is determined, and if it is curved, some coordinate pairs in between are computed. The length of the chain gives a good idea of the number of bacteria involved. A myriad of other complexities are dealt with.

Repositioning functions.

When repositioning the automated motorized stage so that a particular bacterium can be seen under the 100× objective lens, the computer directs the stage to move to the central coordinates of that bacterium: the operator will then see both a low power objective field of the area around the bacterium and a high power objective field of the bacterium itself. If due to drift or other circumstances, the bacterium is not at the center of the low power field, then the operator can interactively move the stage a little to get it in the center when it will be seen in the high power field. The motorized stage moves in 5$\mu$ steps, resulting in a positional accuracy of ±2.5$\mu$, which is more than adequate for relocating a mycobacterium.

When a bacterium on a slide is initially identified as an object to be reviewed from time to time, then of course, the coordinates of that object are stored in the computer as associated with that particular slide. The slide may be taken out of the ATBD unit for continued incubation elsewhere and then at a later time, put back into the ATBD unit. The ATBD unit is so accurate that it can relocate the coordinates of the bacterium in question so that it can be seen again. This procedure can be carried out whenever required and it can be carried out for any bacteria for which the coordinates are known on any particular slide. In this way the ATBD unit is used for processing many different patient specimens where the slides containing the specimens can be taken out for incubation elsewhere and then replaced at the proper time as desired.

The ATBD unit includes several alternative methods for viewing luminescing M.TB. One method is to use the Hi-power TV camera, and continually capture successive images of the same stationary bacterium and average the images in the computer. Coupled with software image enhancement methods, this approach results in the imaging of the luminescing bacterium. Another method is to use an intensified TV camera. The line scan camera is also used. Finally, as mentioned above, for just detecting luminescence, not imaging, the photomultiplier tube is used, where the number of luminescing M.TB in a field is estimated by the value of the integrated intensity of the light. The results reported.

The ATBD unit will have a listing of the x,y coordinates of all the mycobacteria found in its memory, and the list is seen on the computer screen; pointing to any item on the list repositions the stage to display that particular bacterium. Or the computer is directed to display each bacterium, one at a time, one right after the other, so the operator can view each. Pushing a computer key can stop the process for more prolonged viewing. Or if there are too many bacteria on the list, then a random sample is called for and displayed, and so forth. Many more options are available for the operator.

For antibiotic testing, there is a separate 'results program' for each antibiotic that depends on its characteristics. For example, for some antibiotics all that need be done is to wait a prescribed time and review each mycobacteria that had been luminescing, to see if it has been killed. For other antibiotics it might be useful to periodically review each mycobacteria to determine the rate of killing. Thus the 'results program' for sensitivity testing can be tailored to the optimum requirements for each antibiotic.

Of course statistical analyses of the results for a particular patient is easily computed. Statistical results for the collection of all or some patients tested on the ATBD unit can be obtained. Other important items of information can also be computed by the ATBD unit, such as the efficiency of transformation of the mycobacteria by the plasmid. The ATBD unit can be used for other than mycobacteria tuberculosis, such as mycobacteria leprosy, for instance. In any event, it is my objective to make the software easy to adapt to special situations. The results report contains patient information as well.

I claim:

1. An apparatus for improving the efficiency of electroporesis comprising:

(a) an electroporesis chamber containing a plurality of electroporesis electrodes which generates an electroporesis field;

(b) a means for suspending microorganisms within said electroporesis chamber in a fluid that is dialectic;

(c) a means for orienting the said microorganisms within said electroporesis chamber so that their long axis is aligned in the direction of said electroporesis field;

(d) a means for maintaining the end of said microorganisms close to one of said electroporesis electrodes;

(e) a means for adding vectors to said fluid that is dialectic;

(f) a means for applying the electroporesis voltages across said electroporesis electrodes.

2. The apparatus for improving the efficiency of electroporesis in claim 1, wherein said means for orienting the said microorganisms is an electric field created by a continuous orienting voltage applied across said electrodes.

3. The apparatus for improving the efficiency of electroporesis in claim 1, wherein the means for maintaining the end of the said microorganisms close to the said electroporesis electrodes is by trapping the said microorganisms into the pores of a filter where the pores are large enough to allow the said microorganism to rotate, but not so large that the said microorganisms can appreciably move or flow in the said dialectic fluid.

4. The apparatus for improving the efficiency of electroporesis in claim 1, wherein said electroporesis electrodes are transparent so that the said microorganisms can be microscopically viewed through the said electroporesis electrodes.

5. An Apparatus for mycobacterum infection diagnosis comprising:

(a) a means for using a mycobacterum vector to insert a marker that causes the luminescing of individual intact Mycobacterium cells;

(b) a means for locating and viewing under a luminescence detecting microscope said Mycobacterium cells;

(c) a means for detecting luminescence in each intact Mycobacterium cell.

6. The apparatus of claim 5, wherein said Mycobacterium vector is a bacteriophage carrying a genetically encoded luminescing marker.

7. The apparatus of claim 5, wherein said Mycobacterium vector is a plasmid carrying a genetically encoded luminescing marker.

8. The apparatus of claim 5, wherein said Mycobacterium are marked by a fluorescing antibody specific for a Mycobacterium prior to exposure to said Mycobacterium vector.

9. The apparatus of claim 5, wherein electroporesis is utilized to facilitate the marking of said Mycobacterium cells by said Mycobacterium vector.

10. The apparatus of claim 5 wherein said genetically encoded luminescing marker is a luciferase gene.

11. An apparatus for mycobacterum antibiotic sensitivity testing comprising:

(a) a means for using a mycobacterum vector to insert a marker that causes the luminescencing of individual Mycobacterium cells;

(b) a means for locating and viewing under a luminescence detecting microscope said Mycobacterium cells;

(c) a means for detecting luminescence in each intact Mycobacterium cell;

(d) a means for counting the number of luminescing said Mycobacterium cells to assess whether or not there is a positive diagnosis of Mycobacterium induced diseases;

(e) a means for recording coordinates of each of said luminescing Mycobacterium cells;

(f) a means for segregating said luminescing Mycobacterium cells in groups;

(g) a means for exposing said groups to an antibiotic, wherein a different antibiotic is used for each group;

(h) a means for segregating said individual Mycobacterium cells of a said group for viewing under said microscope to determine if each of said Mycobacterium cells is luminseing;

(i) a means to assess for each of said group, sensitivity or resistance of the said Mycobacterium in the group to the said antibiotic, based on a count of the number of said Mycobacterium cells of the group that remain continue to luminesce after a predetermined time depending on the antibiotic being tested.

12. The apparatus of claim 11, wherein said Mycobacterium vector is a bacteriophage carrying a genetically encoded luminescing marker.

13. The apparatus of claim 11, wherein said Mycobacterium vector is a plasmid carrying a genetically encoded luminescing marker.

14. The apparatus of claim 11, wherein said Mycobacterium are marked by a fluorescing antibody specific for a Mycobacterium prior to exposure to said Mycobacterium vector.

15. The apparatus of claim 11, wherein electroporesis is utilized to facilitate the marking of said Mycobacterium by said Mycobacterium vector.

16. The apparatus of claim 11, wherein said genetically encoded luminescing marker is a luciferase gene.

17. A method for Mycobacterium infection diagnosis using individual mycobacterial cells comprising:

(a) inserting a marker that causes the luminescencing of individual Mycobacterium cells by using a Mycobacterium vector;

(b) locating and viewing under a luminescence detecting microscope said Mycobacterium cells;

(c) detecting luminescence in each intact Mycobacterium cell.

18. The method in claim 17, wherein said Mycobacterium vector is a bacteriophage carrying a genetically encoded luminescing marker.

19. The method in claim 17, wherein said Mycobacterium vector is a plasmid carrying a genetically encoded luminescing marker.

20. The method in claim 17, wherein said Mycobacterium are marked by a fluorescing antibody specific for a Mycobacterium prior to exposure to said Mycobacterium vector.

21. The method in claim 17, wherein electroporesis is utilized to facilitate the marking of said Mycobacterium by said Mycobacterium vector.

22. The method in claim 17, wherein said genetically encoded luminescing marker is a luciferase gene.

23. A method for determining Mycobacterium antibiotic sensitivity testing comprising:

(a) inserting a marker that causes the luminescencing of individual Mycobacterium cells using a mycobacterum vector;

(b) locating and viewing under a luminescence detecting microscope said marked Mycobacterium cells;

(c) detecting luminescence in each intact Mycobacterium cell;

(d) counting the number of luminescing said Mycobacterium cells to assess whether or not there is a positive diagnosis of Mycobacterium induced diseases;

(e) recording coordinates of each of said luminescing Mycobacterium cells;

(f) segregating said luminescing Mycobacterium cells in groups;

(g) exposing said groups to an antibiotic, wherein a different antibiotic is used for each group;

(h) segregating said individual Mycobacterium cells of a said group for viewing under said microscope to determine if each Mycobacterium cells is luminseing;

(i) assessing for each group, sensitivity or resistance of the said Mycobacterium cells in said group to the said antibiotic, based on a count of the number of said Mycobacterium cells of said group that continue to luminesce after a predetermined time depending on the antibiotic being tested.

24. The method in claim 23, wherein said Mycobacterium vector is a bacteriophage carrying a genetically encoded luminescing marker.

25. The method in claim 23, wherein said Mycobacterium vector is a plasmid carrying a genetically encoded luminescing marker.

26. The method in claim 23, wherein said Mycobacterium are marked by a fluorescing antibody specific for a Mycobacterium prior to exposure to said Mycobacterium vector.

27. The method in claim 23, wherein electroporesis is utilized to facilitate the marking of said Mycobacterium by said Mycobacterium vector.

28. The method in claim 23, wherein said genetically encoded luminescing marker is a luciferase gene.

29. An automated pattern recognition apparatus for recognizing mycobacterium in the field of view comprising:

(a) an imaging means;

(b) a scanning means using a TV camera or a line scan camera whereby the image intensity profiles of the scanning lines are recorded in a computers memory;

(c) a processing means;

wherein the darker portions of said profiles are distinguished as covers;

wherein the coordinates of the beginning and ending of the said covers is ascertained and recorded in a computer's memory;

wherein the relationship between the said beginning and ending of said covers from successive said scanning lines is analyzed; and wherein said analysis consists of a means for distinguishing between said relationships that represent mycobacterium images and images of non- mycobacterium objects in the image.

30. The apparatus in claim 29, wherein said imaging means is a bright field microscope.

31. The apparatus in claim 29, wherein said imaging means is a phase microscope.

32. The apparatus in claim 29, wherein said imaging means is a dark field microscope.

33. The apparatus in claim 29, wherein said imaging means is a mixed phase/darkfield microscope.

34. The apparatus in claim 29, wherein the sample is treated with a vital stain means so that the images of the mycobacterium are made to appear different than the background in the image.

35. An apparatus for improving the efficiency of the electroporesis process on a specimen of suspended microorganisms comprising:

(a) a chamber, the interior of which is suitable for holding a specimen and the exterior of which is suitable for being placing on a microscope stage;

(b) a plurality of electrodes energisable by at least one power supply;

wherein said electrodes when energized produce an electrostatic field in the fluid filled part of said chamber that rotates microorganisms so their long axis are perpendicular to the surface of the electrodes;

wherein said electrodes when energized produce electroporesis electrical pulses for inserting the plasmid into said microorganisms;

(c) an electric circuit suitable for producing the said electrostatic field and the said electroporesis electrical pulses.

36. The apparatus of claim 35, wherein said chamber is constructed from or lined with a conducting material to be used as electrodes for said electroporesis process.

37. The apparatus of claim 35, wherein said chamber is shaped with flat top and bottom sides with one of said sides is transparent for viewing the said specimen under a microscope, and the other of said side is translucent or transparent to enable light to illuminate the said specimen.

38. The apparatus of claim 35, wherein said interior forms a plurality of group modules so that a portion of the said sample can be held in each module, so that simultaneously each module can be used to test the sensitivity of the microorganisms to an antibiotic different from that tested in the other modules.

39. The apparatus of claim 38, wherein each of said modules is comprised of an input well to receive reagents, a specimen holding pool containing a filter to trap the said microorganisms in the pores of said filter, an output well to dispose of unwanted substances, an input channel connecting the input well to a specimen holding pool, and an output channel connecting the output well to the said specimen holding pool.

40. An apparatus for effectuating the fast Mycobacterium diagnosis and sensitivity testing comprising:

(a) a computer controlled automated microscope for viewing and analyzing microorganisms in the field of view comprising:

(b) a high power microscope objective lens for viewing a field of view consisting of one of the following: (1) a 100×objective; (2) a phase 100×objective;

(c) a light source for illuminating the field of view that can be turned on or off;

(d) a computer controlled motorized microscope stage capable of holding a chamber on said stage;

(e) a means of moving a microorganism by automated means under the said objective lens, then automatically determining the coordinates of the stage corresponding to the microorganism and storing said coordinates in a computer's memory;

(f) a means for automatically relocating said respective microorganisms under the said objective lens by retrieving the coordinates from the computer's memory and then repositioning the said stage to the said corresponding coordinates.

41. The apparatus in claim 40, wherein a light channel is affixed to said object lens for directing the light from the said objective lens to the detectors and image viewers.

42. An apparatus for enabling both immunofluorescence followed by luminescence to be used for identifying a microorganism and then for antibiotic sensitivity testing of microorganisms comprising:

(a) a chamber of a size suitable for being placing on a microscope stage shaped with flat top and bottom sides;

wherein one of said sides is transparent for viewing a specimen under a microscope and at least one side is transparent/translucent to enable light to illuminate the said specimen;

wherein the sides of said chamber form an interior which is subdivided into a plurality of group modules;

wherein a portion of the said sample can be held in each module, so that simultaneously each module can be used to test the sensitivity of the microorganisms to an antibiotic different from that tested in the other modules.

43. The apparatus in claim 42, wherein each of said modules is comprised of an input well to receive reagents, a specimen holding pool containing a filter to trap the said microorganisms in the pores of said filter, an output well to dispose of unwanted substances, an input channel connecting the input well to a specimen holding pool, and an output channel connecting the output well to the said specimen holding pool.

* * * * *